Figure 1:
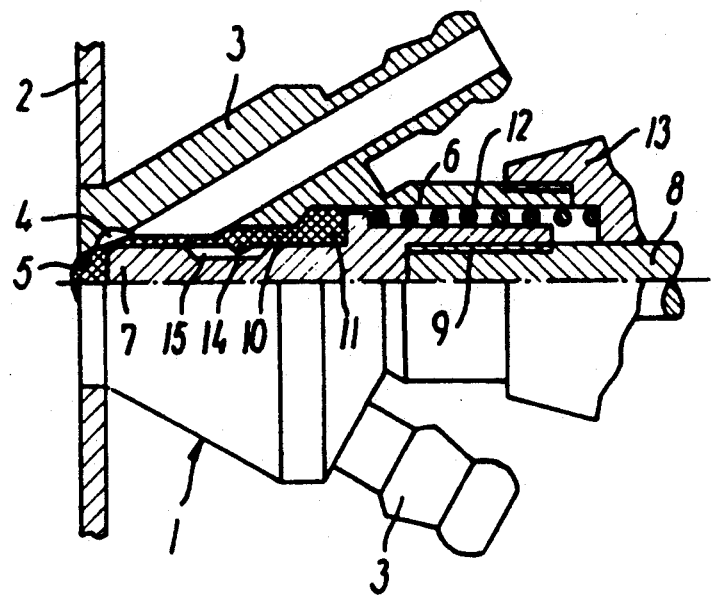

United States Patent [19]

Ottung

[11] Patent Number: 5,246,204
[45] Date of Patent: Sep. 21, 1993

[54] SAMPLING VALVE

[76] Inventor: Kaj Ottung, Askebyvej 8, DK-2830 Virum, Denmark

[21] Appl. No.: 761,991

[22] PCT Filed: Apr. 24, 1989

[86] PCT No.: PCT/DK89/00095
§ 371 Date: Sep. 26, 1991
§ 102(e) Date: Sep. 26, 1991

[87] PCT Pub. No.: WO90/12972
PCT Pub. Date: Nov. 1, 1990

[51] Int. Cl.⁵ .............................................. F16K 7/12
[52] U.S. Cl. ................................. 251/331; 251/335.2; 137/863
[58] Field of Search .................... 251/331, 335.2; 137/863

[56] References Cited

U.S. PATENT DOCUMENTS 4,552,336 11/1985 Pastrone .
4,720,076 1/1988 Hyde .............................. 251/331 X

FOREIGN PATENT DOCUMENTS 147119 4/1984 Denmark .
2732/86 7/1986 Denmark .
445852 7/1986 Sweden .
318753 12/1986 Sweden .
635407 3/1983 Switzerland .

Primary Examiner—Arnold Rosenthal
Attorney, Agent, or Firm—Bacon & Thomas

[57] ABSTRACT

A sampling valve is disclosed comprising a stretchable hollow valve plug mounted on the front end of an axially displaceable valve stem. The plug is provided on its inner surface with a bead projecting into a groove in the stem. When the stem is withdrawn from the valve body for inspection or other purposes, the plug is carried along due to the engagement of the bead with a side wall of the groove.

1 Claim, 1 Drawing Sheet

SAMPLING VALVE

This invention relates to a sampling valve comprising a valve body having an axial bore, a valve stem axially displaceable in the bore, and a stretchable hollow valve plug that is mounted on the valve stem, the valve stem being axially displaceable within the valve plug, the front end of the valve stem pushing the valve plug in its stretched position wherein the latter closes against a valve seat coaxial with the bore and extending from an annular channel communicating with a pair of hose connection branches of the valve body.

Such a valve structure is disclosed in the published documents of Applicant's Danish Patent Application No. 2732/86. An important feature of this valve is that the valve plug is firmly bonded to the wall of the axial bore at least in its area adjacent the annular channel, for the purpose of preventing liquid from penetrating between the valve body and the plug. Such a risk is involved with a previously known sampling valve, cf. Danish Patent Specification No. 147,119, in which the plug is firmly bonded to the forward end portion of the stem and forms a plunger operating in the forward end of the bore.

In the latter case the plug may be withdrawn from the bore together with the valve stem, e.g. for renewal or for allowing the interior of the valve to be inspected, whereas in the former case such a withdrawal or removal of the plug from the bore is more complicated because its bonding to the bore wall must be broken. The plug may be thereby further damaged so that it cannot be used again.

Swiss patent specification No. 635 407 discloses a valve comprising a stretchable hollow valve plug, the front end of a valve stem pushing the valve plug in its stretched position whereby a collar at the open end of the valve plug is forced against an abutting sealing surface and the valve plug closes against a valve seat coaxial with the valve stem.

The sampling valve of the invention differs from the known structures by the feature that the valve plug rests with a collar at its open end against an abutting surface in the bore and in that on the inner surface of the valve plug member a bead is provided which in the mounted position of the member projects into a circumferential groove formed in the valve stem and having an axial length that is sufficient to permit the stretching of the valve plug from its open to its closed position.

Under normal operating conditions the groove of the valve stem does not prevent the bead from moving axially backwards and forwards relative to the stem when the plug is stretched and allowed to retract, respectively. However, when it is desired to remove the plug for inspection or other purposes, the stem may simply be withdrawn axially out of the bore, thereby causing the plug to be carried along after the bead has come into contact with the forward side wall of the groove. When the plug has got clear of the bore, it may easily be snapped free from the stem, if so desired.

The invention will now be more fully described with reference to the drawing, in which FIG. 1 is a side elevation and axial section of a preferred embodiment of the valve in its closed position, and FIG. 2 a similar view of the valve when open.

In the illustrated embodiment the valve comprises a body or casing 1 adapted to be firmly mounted in the wall 2 of a tank or pipe containing a liquid from which samples shall be taken from time to time. A pair of hose connection branches 3, communicate at their inner ends with an annular channel 4 adjacent a central valve seat 5.

A bore 6 in body 1 is co-axial with the valve seat, and in this bore a valve stem is axially displaceable. The stem comprises a front or lower portion 7 and a back or upper portion 8 with a threaded connection 9 therebetween.

A stretchable hollow valve plug 10 fits into the forward end of the bore 6 and rests with a collar 11 at its open end against a shoulder in the bore. The plug 10 surrounds the forward end of the stem portion 7 which in FIG. 1 is urged to the left by a helical compression spring 12 so that the plug 10 is stretched longitudinally and with its forward end or bottom is held in close contact against the valve seat 5. In this position a small amount of liquid may be withdrawn from the tank or pipe by means of a hypodermic needle inserted through one of the branches and forced through the closed end of the plug 10.

Figure 2:
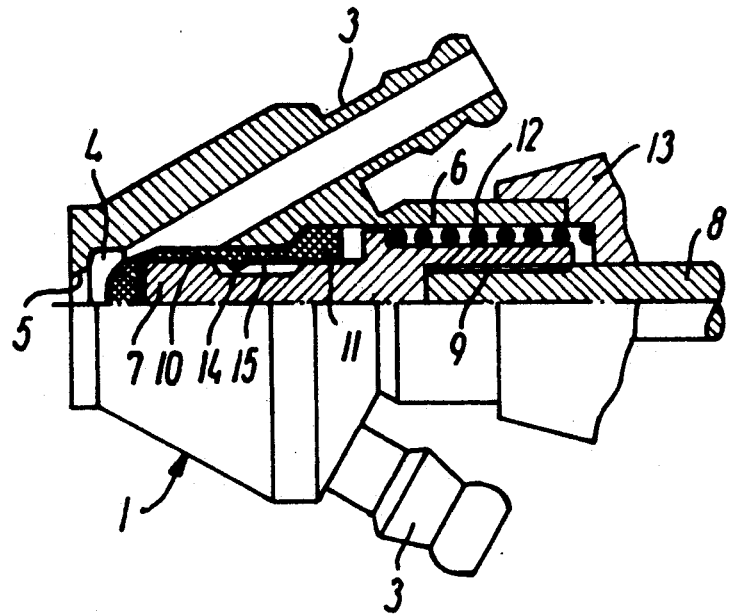

The upper portion 8 of the stem is associated with a manual control, not shown, which is detachably connected with the valve body by means of a union nut 13 and is operative to displace the stem 7, 8 backwards against the force of the spring 12, so that the plug 10 is allowed to contract to the open position illustrated in FIG. 2.

On the inner side of the plug 10 an annular bead 14 is provided which projects into a circumferential groove 15 in stem portion 7. The axial length of this groove is such that it offers sufficient clearance for the bead when the plug is stretched and allowed to contract as explained above.

When it is desired to inspect the interior of the valve or possibly exchange plug 10, nut 13 may be loosened and stem 7, 8 retracted from the bore 6 whereby the plug 10 is carried along due to the contact between bead 14 and the forward side wall of groove 15.

I claim:

1. A sampling valve comprising a valve body having an axial bore and an annular channel communicating with a pair of hose connection branches of the valve body; a valve stem axially displaceable in the bore, said valve stem having a circumferential groove formed therein; and a stretchable hollow valve plug having an open end and a collar at its open end, said valve plug mounted on the valve stem; the valve stem being axially displaceable within the valve plug, the front end of the valve stem pushing the valve plug in its stretched position wherein the latter closes against a valve seat coaxial with the bore and extending from the channel; and wherein the valve plug rests with the collar at its open end and against an abutting surface in the bore and wherein, on the inner surface of the valve plug member, a bead is provided which in the mounted position of the member projects into the circumferential groove formed in the valve stem and said groove has an axial length that is sufficient to permit the stretching of the valve plug from its open to its closed position.

* * * * *